(12) United States Patent
Gellman et al.

(10) Patent No.: US 9,433,488 B2
(45) Date of Patent: *Sep. 6, 2016

(54) MEDICAL SLINGS

(71) Applicant: Boston Scientific Scimed, Inc., Maple Grove, MN (US)

(72) Inventors: Barry N. Gellman, North Eastern, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/549,200

(22) Filed: Nov. 20, 2014

(65) Prior Publication Data

US 2015/0080645 A1 Mar. 19, 2015

Related U.S. Application Data

(63) Continuation of application No. 13/665,312, filed on Oct. 21, 2012, now Pat. No. 8,915,872, which is a continuation of application No. 13/213,774, filed on Aug. 19, 2011, now Pat. No. 8,303,526, which is a (Continued)

(51) Int. Cl.
*A61F 5/00* (2006.01)
*A61F 2/00* (2006.01)

(Continued)

(52) U.S. Cl.
CPC ....... *A61F 2/0045* (2013.01); *A61B 17/00234* (2013.01); *A61B 17/06109* (2013.01); *A61F 2/0063* (2013.01); *A61B 17/3468* (2013.01); *A61B 2017/00805* (2013.01); *A61B 2017/06019* (2013.01); *A61B 2017/06042* (2013.01);

(Continued)

(58) Field of Classification Search
CPC .............. A61F 2/0045; A61F 2/0063; A61F 2210/0004; A61F 2250/0078; A61F 2250/0097; A61F 2/0095; A61F 2240/001; A61F 2/0036; A61F 2002/30708; A61F 2250/0084; A61F 6/08; A61F 2013/530481; A61F 13/4756; A61F 13/49017; A61F 13/49413; A61F 13/4942; A61F 13/4946; A61F 13/51113; A61F 13/534; A61F 13/53713; A61F 2002/0072; A61F 2013/15121; A61F 2013/4512; A61B 2017/00805
USPC .................................. 128/885, 886; 600/29
See application file for complete search history.

(56) References Cited

U.S. PATENT DOCUMENTS 2,253,132 A 8/1941 Malson
2,400,251 A 5/1946 Nagel (Continued)

FOREIGN PATENT DOCUMENTS

DE 703123 C 3/1941
DE 4323578 A1 1/1994

(Continued)

OTHER PUBLICATIONS

Non-Final Office Action for U.S. Appl. No. 13/665,312, mailed on Oct. 10, 2013, 6 pages.

(Continued)

*Primary Examiner* — Michael Brown
(74) *Attorney, Agent, or Firm* — Brake Hughes Bellermann LLP

(57) ABSTRACT

A medical sling made from material that is suitably shaped for use in a medical application has sides, portions of which are smoothed to prevent abrasion of surrounding tissue.

18 Claims, 2 Drawing Sheets

Related U.S. Application Data continuation of application No. 13/007,090, filed on Jan. 14, 2011, now Pat. No. 8,007,452, which is a continuation of application No. 12/843,478, filed on Jul. 26, 2010, now abandoned, which is a continuation of application No. 11/159,988, filed on Jun. 23, 2005, now Pat. No. 7,762,969, which is a continuation of application No. 10/092,872, filed on Mar. 7, 2002, now Pat. No. 6,953,428.

(60) Provisional application No. 60/274,843, filed on Mar. 9, 2001, provisional application No. 60/286,863, filed on Apr. 26, 2001.

(51) Int. Cl.
*A61B 17/00* (2006.01)
*A61B 17/06* (2006.01)
*A61B 17/34* (2006.01)

(52) U.S. Cl.
CPC ........... *A61B2017/06052* (2013.01); *A61B 2017/06076* (2013.01); *A61B 2017/06171* (2013.01); *A61F 2230/0019* (2013.01); *A61F 2240/001* (2013.01); *A61F 2250/0087* (2013.01); *Y10S 128/25* (2013.01); *Y10T 29/49995* (2015.01)

(56) References Cited

U.S. PATENT DOCUMENTS

| | | | |
|---|---|---|---|
| 2,631,585 A | 3/1953 | Siebrandt | |
| 2,671,444 A | 3/1954 | Pease | |
| 2,917,878 A | 12/1959 | Carnarius et al. | |
| 2,973,859 A | 3/1961 | Schladermundt et al. | |
| 3,054,406 A | 9/1962 | Usher | |
| 3,124,136 A | 3/1964 | Usher | |
| 3,364,200 A | 1/1968 | Ashton et al. | |
| 3,580,313 A | 5/1971 | Mcknight | |
| 3,642,565 A | 2/1972 | Ogata et al. | |
| 3,657,744 A | 4/1972 | Ersek et al. | |
| 3,666,750 A | 5/1972 | Briskin et al. | |
| 3,705,575 A | 12/1972 | Edwards | |
| 3,710,592 A | 1/1973 | Scow | |
| 3,710,795 A | 1/1973 | Higuchi et al. | |
| 3,849,044 A | 11/1974 | Ando et al. | |
| 3,875,937 A | 4/1975 | Schmitt | |
| 3,937,223 A | 2/1976 | Roth | |
| 4,085,756 A | 4/1978 | Weaver | |
| 4,156,424 A | 5/1979 | Burgin | |
| 4,172,458 A | 10/1979 | Pereyra | |
| 4,193,137 A | 3/1980 | Heck | |
| 4,217,890 A | 8/1980 | Owens | |
| 4,254,763 A | 3/1981 | McCready et al. | |
| 4,347,847 A | 9/1982 | Usher | |
| 4,363,319 A | 12/1982 | Altshuler | |
| 4,367,816 A | 1/1983 | Wilkes | |
| 4,400,833 A | 8/1983 | Kurland | |
| 4,409,974 A | 10/1983 | Freedland | |
| 4,414,967 A | 11/1983 | Shapiro | |
| 4,445,898 A | 5/1984 | Jensen | |
| 4,452,245 A | 6/1984 | Usher | |
| D275,790 S | 10/1984 | Marlowe | |
| 4,520,821 A | 6/1985 | Schmidt et al. | |
| 4,545,374 A | 10/1985 | Jacobson | |
| 4,549,545 A | 10/1985 | Levy | |
| 4,592,339 A | 6/1986 | Kuzmak et al. | |
| 4,617,916 A | 10/1986 | Levahn et al. | |
| 4,633,873 A | 1/1987 | Dumican et al. | |
| 4,652,264 A | 3/1987 | Dumican | |
| 4,655,221 A | 4/1987 | Devereux | |
| 4,741,330 A | 5/1988 | Hayhurst | |
| 4,769,038 A | 9/1988 | Bendavid et al. | |
| 4,776,337 A | 10/1988 | Palmaz et al. | |
| 4,784,126 A | 11/1988 | Hourahane | |
| 4,838,884 A | 6/1989 | Dumican et al. | |
| 4,854,316 A | 8/1989 | Davis | |
| 4,857,041 A | 8/1989 | Annis et al. | |
| 4,872,451 A | 10/1989 | Moore et al. | |
| 4,873,977 A | 10/1989 | Avant et al. | |
| 4,905,692 A | 3/1990 | More | |
| 4,911,165 A | 3/1990 | Lennard et al. | |
| 4,938,760 A | 7/1990 | Burton et al. | |
| 4,945,897 A | 8/1990 | Greenstein et al. | |
| 4,969,892 A | 11/1990 | Burton et al. | |
| 4,973,300 A | 11/1990 | Wright | |
| 4,986,831 A | 1/1991 | King et al. | |
| 4,997,434 A | 3/1991 | Seedhom et al. | |
| 5,002,551 A | 3/1991 | Linsky et al. | |
| 5,012,822 A | 5/1991 | Schwarz | |
| 5,013,292 A | 5/1991 | Lemay | |
| 5,019,032 A | 5/1991 | Robertson | |
| 5,019,096 A | 5/1991 | Fox et al. | |
| 5,026,376 A | 6/1991 | Greenberg | |
| 5,026,398 A | 6/1991 | May et al. | |
| 5,027,793 A | 7/1991 | Engelhardt et al. | |
| D319,877 S | 9/1991 | O'Neal-Cox | |
| 5,064,434 A | 11/1991 | Haber | |
| 5,112,344 A | 5/1992 | Petros | |
| 5,122,130 A | 6/1992 | Keller | |
| 5,122,155 A | 6/1992 | Eberbach | |
| 5,147,374 A * | 9/1992 | Fernandez | 606/151 |
| 5,149,329 A | 9/1992 | Richardson | |
| 5,174,278 A | 12/1992 | Babkow | |
| 5,176,692 A | 1/1993 | Wilk et al. | |
| 5,178,630 A | 1/1993 | Schmitt | |
| 5,195,542 A | 3/1993 | Gazielly et al. | |
| 5,234,457 A | 8/1993 | Andersen | |
| 5,252,701 A | 10/1993 | Jarrett et al. | |
| 5,254,133 A | 10/1993 | Seid | |
| 5,256,133 A | 10/1993 | Spitz | |
| 5,257,692 A | 11/1993 | Heacox | |
| 5,258,000 A | 11/1993 | Gianturco | |
| 5,263,969 A | 11/1993 | Phillips | |
| 5,289,963 A | 3/1994 | Mcgarry et al. | |
| 5,290,217 A | 3/1994 | Campos | |
| 5,292,328 A | 3/1994 | Hain et al. | |
| 5,304,220 A | 4/1994 | Maginot | |
| 5,308,349 A | 5/1994 | Mikhail | |
| 5,328,077 A | 7/1994 | Lou | |
| 5,333,624 A | 8/1994 | Tovey et al. | |
| 5,337,736 A | 8/1994 | Reddy | |
| 5,354,292 A | 10/1994 | Braeuer et al. | |
| 5,356,064 A | 10/1994 | Green et al. | |
| 5,358,492 A | 10/1994 | Feibus | |
| 5,362,294 A | 11/1994 | Seitzinger | |
| 5,364,002 A | 11/1994 | Green et al. | |
| 5,366,460 A | 11/1994 | Eberbach | |
| 5,366,479 A | 11/1994 | Mcgarry et al. | |
| 5,368,602 A | 11/1994 | De La Torre | |
| 5,370,650 A | 12/1994 | Tovey et al. | |
| 5,381,943 A | 1/1995 | Allen et al. | |
| 5,383,477 A | 1/1995 | Dematteis | |
| 5,397,330 A | 3/1995 | Mikhail | |
| 5,397,332 A | 3/1995 | Kammerer et al. | |
| 5,425,737 A | 6/1995 | Burbank et al. | |
| 5,425,984 A | 6/1995 | Kennedy et al. | |
| 5,437,603 A | 8/1995 | Cerny et al. | |
| 5,441,508 A | 8/1995 | Gazielly et al. | |
| 5,451,235 A | 9/1995 | Lock et al. | |
| 5,474,543 A | 12/1995 | Mckay | |
| 5,507,796 A | 4/1996 | Hasson | |
| 5,527,341 A | 6/1996 | Gogolewski et al. | |
| 5,527,342 A | 6/1996 | Pietrzak et al. | |
| 5,536,251 A | 7/1996 | Evard et al. | |
| 5,544,664 A | 8/1996 | Benderev et al. | |
| 5,549,619 A | 8/1996 | Peters et al. | |
| 5,549,967 A | 8/1996 | Gstrein et al. | |
| 5,562,679 A | 10/1996 | Valtchev | |
| 5,569,273 A | 10/1996 | Titone et al. | |
| 5,569,300 A | 10/1996 | Redmon | |
| 5,582,188 A | 12/1996 | Benderev et al. | |
| 5,591,163 A | 1/1997 | Thompson | |
| 5,611,515 A | 3/1997 | Benderev et al. | |

(56) References Cited

U.S. PATENT DOCUMENTS

| | | | |
|---|---|---|---|
| 5,618,260 A | 4/1997 | Caspar et al. | |
| 5,620,012 A | 4/1997 | Benderev et al. | |
| 5,634,931 A | 6/1997 | Kugel | |
| 5,634,944 A | 6/1997 | Magram | |
| 5,641,502 A | 6/1997 | Skalla et al. | |
| 5,641,566 A | 6/1997 | Kranzler et al. | |
| 5,643,288 A | 7/1997 | Thompson | |
| 5,643,596 A | 7/1997 | Pruss et al. | |
| 5,645,849 A | 7/1997 | Pruss et al. | |
| 5,645,915 A | 7/1997 | Kranzler et al. | |
| 5,660,854 A | 8/1997 | Haynes et al. | |
| 5,681,265 A | 10/1997 | Maeda et al. | |
| 5,681,310 A | 10/1997 | Yuan et al. | |
| 5,690,655 A | 11/1997 | Hart et al. | |
| 5,697,931 A | 12/1997 | Thompson | |
| 5,700,286 A | 12/1997 | Tartaglia et al. | |
| 5,707,647 A | 1/1998 | Dunn et al. | |
| 5,711,960 A | 1/1998 | Shikinami | |
| 5,733,337 A | 3/1998 | Carr et al. | |
| 5,735,849 A | 4/1998 | Baden et al. | |
| 5,755,726 A | 5/1998 | Pratt et al. | |
| 5,766,221 A | 6/1998 | Benderev et al. | |
| 5,769,864 A | 6/1998 | Kugel | |
| 5,776,184 A | 7/1998 | Tuch | |
| 5,807,403 A | 9/1998 | Beyar et al. | |
| 5,813,975 A | 9/1998 | Valenti | |
| 5,816,258 A | 10/1998 | Jervis | |
| 5,824,029 A | 10/1998 | Weijand et al. | |
| 5,824,082 A | 10/1998 | Brown | |
| 5,836,314 A | 11/1998 | Benderev et al. | |
| 5,836,961 A | 11/1998 | Kieturakis et al. | |
| 5,840,011 A | 11/1998 | Landgrebe et al. | |
| 5,899,909 A | 5/1999 | Claren et al. | |
| 5,916,225 A | 6/1999 | Kugel | |
| 5,922,026 A | 7/1999 | Chin | |
| 5,934,283 A | 8/1999 | Willem et al. | |
| 5,997,554 A | 12/1999 | Thompson | |
| 6,010,447 A * | 1/2000 | Kardjian | 600/29 |
| 6,039,686 A | 3/2000 | Kovac | |
| 6,042,534 A | 3/2000 | Gellman et al. | |
| 6,042,536 A | 3/2000 | Tihon et al. | |
| 6,042,583 A | 3/2000 | Thompson et al. | |
| 6,053,935 A | 4/2000 | Brenneman et al. | |
| 6,059,801 A | 5/2000 | Samimi | |
| 6,068,591 A | 5/2000 | Bruckner et al. | |
| 6,077,216 A | 6/2000 | Benderev et al. | |
| 6,090,116 A | 7/2000 | D'Aversa et al. | |
| 6,099,547 A | 8/2000 | Gellman et al. | |
| 6,102,921 A | 8/2000 | Zhu et al. | |
| 6,110,101 A | 8/2000 | Tihon et al. | |
| 6,117,067 A | 9/2000 | Gil-Vernet | |
| 6,168,801 B1 | 1/2001 | Heil et al. | |
| 6,200,330 B1 | 3/2001 | Benderev et al. | |
| 6,221,005 B1 | 4/2001 | Bruckner et al. | |
| 6,224,616 B1 | 5/2001 | Kugel | |
| 6,299,607 B1 | 10/2001 | Osborn et al. | |
| 6,306,079 B1 | 10/2001 | Trabucco | |
| 6,355,065 B1 | 3/2002 | Gabbay | |
| 6,423,080 B1 | 7/2002 | Gellman et al. | |
| 6,475,139 B1 | 11/2002 | Miller | |
| 6,517,566 B1 | 2/2003 | Hovland et al. | |
| 6,530,879 B1 | 3/2003 | Adamkiewicz | |
| 6,638,210 B2 | 10/2003 | Berger | |
| 6,953,428 B2 * | 10/2005 | Gellman | A61B 17/00234 600/29 |
| 7,762,969 B2 * | 7/2010 | Gellman | A61B 17/00234 600/30 |
| 8,007,452 B2 * | 8/2011 | Gellman | A61B 17/00234 600/30 |
| 8,303,526 B2 * | 11/2012 | Gellman | A61B 17/00234 600/30 |
| 8,915,872 B2 * | 12/2014 | Gellman | A61B 17/00234 600/29 |
| 2002/0007222 A1 | 1/2002 | Desai | |
| 2002/0143234 A1 | 10/2002 | LoVuolo | |
| 2003/0023136 A1 | 1/2003 | Raz et al. | |
| 2003/0023138 A1 | 1/2003 | Luscombe | |
| 2003/0179958 A1 | 9/2003 | Chiang et al. | |
| 2004/0015048 A1 | 1/2004 | Neisz et al. | |
| 2007/0273662 A1 | 11/2007 | Lian et al. | |
| 2008/0165141 A1 | 7/2008 | Christie | |
| 2009/0064047 A1 | 3/2009 | Shim et al. | |
| 2009/0122018 A1 | 5/2009 | Vymenets et al. | |
| 2009/0140986 A1 | 6/2009 | Karkkainen et al. | |
| 2009/0243898 A1 | 10/2009 | Iorfida et al. | |
| 2009/0256817 A1 | 10/2009 | Perlin et al. | |
| 2009/0265627 A1 | 10/2009 | Kim et al. | |
| 2009/0309768 A1 | 12/2009 | Pihlaja | |
| 2010/0004029 A1 | 1/2010 | Kim | |
| 2010/0064261 A1 | 3/2010 | Andrews et al. | |
| 2010/0259484 A1 | 10/2010 | Jo | |
| 2010/0302155 A1 | 12/2010 | Sands et al. | |
| 2011/0009169 A1 | 1/2011 | Kim | |
| 2011/0106439 A1 | 5/2011 | Huang et al. | |
| 2011/0231796 A1 | 9/2011 | Vigil | |
| 2011/0263298 A1 | 10/2011 | Park | |
| 2011/0302532 A1 | 12/2011 | Missig | |
| 2012/0112024 A1 | 5/2012 | Gotzl | |
| 2012/0112025 A1 | 5/2012 | Smeenk | |
| 2012/0112026 A1 | 5/2012 | Crawford | |
| 2012/0324381 A1 | 12/2012 | Cohen et al. | |
| 2013/0234949 A1 | 9/2013 | Chornenky | |
| 2013/0303839 A1 | 11/2013 | Gellman et al. | |

FOREIGN PATENT DOCUMENTS

| | | |
|---|---|---|
| EP | 0625417 A1 | 11/1994 |
| EP | 0692225 A2 | 1/1996 |
| EP | 703123 A2 | 3/1996 |
| EP | 0599772 B1 | 2/1997 |
| EP | 0334046 B1 | 6/1997 |
| EP | 0677297 B1 | 12/2000 |
| EP | 0778749 B1 | 12/2000 |
| GB | 0725343 A | 3/1955 |
| GB | 2268690 A | 1/1994 |
| JP | 6-114067 A | 4/1994 |
| SE | 503271 C2 | 4/1996 |
| SE | 506164 C2 | 11/1997 |
| SU | 610512 A1 | 6/1978 |
| WO | 88/01853 A1 | 3/1988 |
| WO | 92/16152 A1 | 10/1992 |
| WO | 93/10715 A2 | 6/1993 |
| WO | 93/10731 A1 | 6/1993 |
| WO | 93/19678 A2 | 10/1993 |
| WO | 94/19029 A1 | 9/1994 |
| WO | 94/28799 A1 | 12/1994 |
| WO | 96/06567 A1 | 3/1996 |
| WO | 96/28083 A1 | 9/1996 |
| WO | 97/13465 A1 | 4/1997 |
| WO | 97/30638 A1 | 8/1997 |
| WO | 97/43982 A1 | 11/1997 |
| WO | 98/12971 A1 | 4/1998 |
| WO | 98/35616 A1 | 8/1998 |
| WO | 00/66030 A1 | 11/2000 |
| WO | 00/74594 A1 | 12/2000 |
| WO | 00/74633 A2 | 12/2000 |
| WO | 02/19945 A2 | 3/2002 |
| WO | 03/007847 A1 | 1/2003 |

OTHER PUBLICATIONS

Non-Final Office Action for U.S. Appl. No. 13/665,312, mailed on Apr. 25, 2014, 6 pages.

Notice of Allowance for U.S. Appl. No. 13/665,312, mailed on Aug. 18, 2014, 5 Pages.

Notice of Allowance for Canadian Patent Application 2,439,212, mailed on Jun. 4, 2013, 1 Page.

Tension-Free Support for Incontinence, 1, 2, 3, 4, 5 Years of Proven Performance, Lasting freedom for your SUI patients, Gynecare TVT, 2002, 6 pages.

"The essence of a contemporary synthetic sling self-anchoring complete adjustability elastic", Safyre Autofixation System, Promedon, 2002, 4 pages.

(56) References Cited

OTHER PUBLICATIONS

SPARCTM, "Sling System for Stress Urinary Incontinence", American Medical System, Inc., Minnetonka.
Araki et al., "The Loop-Loosening Procedure for Urination Difficulties After Stamey Spension of the Vesical Neck", Journal of Urology, 144, Aug. 1990, pp. 319-323.
Bayer et al., "A new approach to primary strengthening of colostomy with Marlex mesh to prevent paracolostomy hernia", Surgery, Gynecology and Obstetrics, 163, 1986, pp. 579-580.
Beck et al., "A 25-Year Experience with 519 Anterior Colporrhaphy Procedure", Obstetrics and Gynecology, 78, 1991, pp. 1011-1018.
Benderev, "A New Endoscopic Bladder Neck Suspension for the Outpatient Treatment of Stress Urinary Incontinence", (video v-40), Journal of Urology, 149:197A, 1993.
Benderev, TV, "Anchor Fixation and Other Modifications of Endoscopic Bladder Neck Suspension", Journal of Urology, 40, Nov. 1992, pp. 409-418.
Benderev, TV, "A Modified Percutaneos Outpatient Bladder Neck Suspension System", Journal of Urology, 152, Dec. 1994, pp. 2316-2320.
Blaivas et al., "Pubovaginal Fascial Sling for the Treatment of Complicated Stress Urinary Incontinence", Journal of Urology, 145, Jun. 1991, pp. 1214-1218.
Blaivas et al., "Successful Pubovaginal Sling Surgery", Contemporary Urology, 1993, pp. 40-63.
Schaeffer, "Endoscopic suspension of vesical neck for urinary incontinence", Urology, 23:, 1984, pp. 484-494.
Schatzker et al., "The Rationale of Operative Fracture Care", Springer-Verlag, Berlin, 1987, 159 pages.
Parra et al., "Experience with a Simplified Technique for the Treatment of Female Stress Urinary Incontinence", British Journal of Urology, vol. 66, Issue 6, Dec. 1990, pp. 615-617.
Spencer et al., "A comparison of Endoscopic Suspension of the Vesical Neck With Suprapublic Vesicourethropexy for Treatment of Stress Urinary Incontinence", The Journal of Urology, 137(3), Apr. 1987, pp. 411-415.
Stamey, Thomas A., "Endoscopic Suspension of the Vesical Neck", Surgery of Female Incontinence, 1986, pp. 115-132.
Stamey, "Endoscopic Suspension of the Vesical Neck for Urinary Incontinence", Surgery, Gynecology and Obstetrics, 136, 1973, pp. 547-554.
Stamey, "Endoscopic Suspension of the Vesical Neck for Urinary Incontinence in Females: Report on 203 Consecutive patients", Ann. Surg., 192, 1980, pp. 465-471.
Trockman et al., "Modified Pereyra Bladder Neck Suspension: 10-year mean follow-up using outcomes analysis in 125 Patients", Journal of Urology, 154, 1995, pp. 1841-1847.
Ulmsten et al., "An Ambulatory Surgical Procedure Under Local Anesthesia for Treatment of Female Urinary Incontinence", International Urogynecology Journal, vol. 7, Issue 2,, 1996, pp. 81-86.
Vasavada et al., "Incisionless Pubovaginal Fascial Sling using Transvaginal Bone Anchors for the Treatment", Digital Urology Journal (http://www.duj.com/ Article/Raz/Raz.html), Jul. 24, 2001.
Webster, "Female Urinary Incontinence", Urologic Surgery J.B. Lippincott Company: Philadelphia, 1983, pp. 665-679.
Webster, "Voiding dysfunction following cystourethropexy: Its evaluation and management", J. Urology, 144, 1990, pp. 670-673.
Winter, "Peripubic urethropexy for urinary stress incontinence in women", Urology, 20, 1982, pp. 408-411.
Zacharin, R F., "Abdominoperineal Urethral Suspension in the Management of Recurrent Stress Incontinence of Urine—a 15-year Experience", Obstetrics Gynecology, 62(5), Nov. 1983, pp. 644-654.
Petros et al., "Ambulatory Surgery for Urinary Incontinence and Vaginal Prolapse", The Medical Journal of Australia, vol. 161, Jul. 18, 1994, pp. 171-172.
Zimmern et al., "Transvaginal Closure of the Bladder Neck", Seminars in Urology, 4, 1986, pp. 30-32.
Petros, P. P., "The Intravaginal Slingplasty Operation, a Minimally Invasive Technique for Cure of Urinary Incontinence in the Female", Australian and New Zealand Journal of Obstetrics and Gynaecology, vol. 36, Issue 4, Nov. 1996, pp. 453-461.
IVS Tunneller—A Universal Instrument for Intra-Vaginal Tape Placement, Tyco Healthcare UK Limited, Gosport-Hampshire, UK.
"About LifeCell", http://www.lifecell.com/about/science.cfm, Jul. 24, 2001, 2 pages.
Cruikshank et al., "Anterior Vaginal Wall Culdeplasty at Vaginal Hysterectomy to Prevent Posthysterectomy Anterior Vaginal Wall Prolapse", American Journal of Obstretrics and Gynecology, 174, Jun. 1996, pp. 1863-1869.
Cruikshank, SH, "Reconstructive Procedures for the Gynecologic Surgeon", American Journal of Obstetrics and Gynecology, 168, Feb. 1993, pp. 469-475.
Delancey, "Structural Support of the urethra as it Relates to Stress Urinary Incontinence: The Hammock Hypothesis", American Journal of Obstetrics and Gynecology, 170, Jun. 1994, pp. 1713-1723.
Ethicon Sarl, "Gynecare TVT—The Tension-Free Solution to Female Incontinence", Switzerland, 4 pages.
Falconer et al., "Clinical Outcome and Changes in Connective Tissue metabolism After Intravaginal Slingplasty in Stress Incontinent Women", International Urogynecology Journal, vol. 7, Issue 3, 1996, pp. 133-137.
Forneret et al., "Cost-Effective Treatment of Female Stress Urinary Incontinence: Modified Pereyra Bladder Neck Suspension", Urology, Apr. 25, 1985, pp. 365-367.
Gittes et al., "No-Incision Pubovaginal Suspension for Stress Incontinence", Journal of Urology, 138(3), Sep. 1987, pp. 568-570.
Guidoin et al., "Collagen coatings as biological sealants for textile arterial prostheses", Biomaterials, 10, 1989, pp. 156-165.
Raz, S, "Modified Bladder Neck Suspension for Female Stress Incontinence", Urology 17(1), Feb. 1981, pp. 82-85.
Hancock et al., "Transpubic Suspension of the Bladder Neck for Urinary Incontinence", Journal of Urology, 123(5), May 1980, pp. 667-668.
Hoffman, "Transvestibular Retropubic Bladder Neck Suspension: A pilot study", Journal of Reproductive Medicine, 40(3), Mar. 1995, pp. 181-184.
Iglesia et al., "The Use of Mesh in Gynecologic Surgery", Journal of Int. Urogynecol, 8(2), 1997, pp. 105-115.
Richarson et al., "Treatment of Stress Urinary Incontinence due to Paravaginal Fascial Defect", Obstretics Gynecology, 57(3), Mar. 1981, pp. 357-362.
Kovac et al., "Pubic Bone Suburethral Stabilization Sling for Recurrent Urinary Incontinence", Obstetrics and Gynecology, 89(4), Apr. 1997, pp. 624-627.
Leach et al., "Bone Fixation Technique for Transvaginal Needle Suspension", Urology, 31, 1988, pp. 388-390.
Leach et al., "Modified Pereyra Bladder Neck Suspension After Previously Failed anti-Incontinence Surgery: Surgical Technique and Results With Long-Term Follow-Up", Urology, 23(4), Apr. 1984, pp. 359-362.
Mascio, "Therapy of Urinary Stress Incontinence in Women Women Using Mitek® GII Anchors", Mitek® Brochure, 1993, 3 pages.
Pereyra, "A Simplified Surgical Procedure for the Correction of Stress Incontinence in Women", West. J. Surg. Obstetrics and Gynecology, 1959, pp. 223-226.
Mattox et al., "Modification of the Miya Hook in Vaginal Colpopexy", The Journal of Reproductive Medicine, 40(10), Oct. 1995, pp. 681-683.
McGuire, "The Sling Procedure for Urinary Stress Incontinence, Profiles in Urology—The Sling Procedure for Urinary Stress Incontinence", 17 pages.
McKiel et al., "Marshall-Marchetti Procedure: Modification", The Journal of Urology 96(5), Dec. 1966, pp. 737-7399.
Mitchell, J. P., "Hook Needle and Retractor for Posterior Urethroplasty", Journal of Urology, 42(5), Oct. 1970, pp. 599-600.
Nativ et al., "Bladder Neck Suspension in Bone Anchors for the Treatment of Female Stress Incontinence", ASAIO Journal, 43(3), May-Jun. 1997, pp. 204-208.
Nichols, "Identification of Pubourethral Ligaments and Their Role in Transvaginal Surgical Correction of Stress Incontinence", American J. Obstet. Gynecology, 115 (1), Jan. 1973, pp. 123-128.
Richmond et al., "Modification of the Bankart Reconstruction with a Suture Anchor: Report of a New Technique", The American Journal of Sports Medicine, 19(4), Jul.-Aug. 1991, pp. 343-346.

\* cited by examiner

MEDICAL SLINGS

CROSS-REFERENCE TO RELATED APPLICATIONS

This application is a continuation of U.S. application Ser. No. 13/665,312, filed on Oct. 21, 2012, which is a continuation of U.S. application Ser. No. 13/213,774, filed on Aug. 19, 2011, now U.S. Pat. No. 8,303,526, which is a continuation of U.S. application Ser. No. 13/007,090, filed on Jan. 14, 2011, now U.S. Pat. No. 8,007,452, which is a continuation of U.S. application Ser. No. 12/843,478, filed on Jul. 26, 2010, now abandoned, which is a continuation of U.S. application Ser. No. 11/159,988, filed on Jun. 23, 2005, now U.S. Pat. No. 7,762,969, which is a continuation of U.S. application Ser. No. 10/092,872, filed on Mar. 7, 2002, now U.S. Pat. No. 6,953,428, which claims the benefit of U.S. Provisional Application No. 60/274,843, filed on Mar. 9, 2001 and U.S. Provisional Application No. 60/286,863, filed on Apr. 26, 2001, the disclosures of which are incorporated by reference herein in their entirety.

TECHNICAL FIELD

This invention generally relates to surgical mesh for use as a medical sling, such as a pelvic floor repair mesh, methods of making such mesh, kits including such mesh, and methods of treating or reinforcing a damaged, prolapsed, weakened or herniated portion of a patient's body using such mesh.

BACKGROUND INFORMATION

Surgical prosthetic mesh has been used to treat or reinforce tissues or organs which have been damaged, prolapsed, weakened, or otherwise herniated, such as in the conditions rectocele, cystocele, enterocele, vaginal prolapse, and protocele, for example. A prolapse refers to the slipping down of an organ or organ part from its normal position. For example, a prolapse of the rectum refers to the protrusion of the inner surface of the rectum through the anus. Rectocele is the prolapse of the rectum into the perineum. A prolapse of the uterus refers to the falling of the uterus into the vagina due to stretching and laxity of its supporting structures. Vaginal vault prolapse refers to the prolapse of the cephalad extreme of the vaginal canal toward, through, and beyond the introitus. Cystocele (i.e., vesicocele) is a hernia formed by the downward and backward displacement of the urinary bladder toward the vaginal orifice, due most commonly to weakening of the musculature during childbirth. However, any abnormal descent of the anterior vaginal wall and bladder base at rest or with strain is considered cystocele. Enterocele is a hernia of the intestine, though the term is also used to refer specifically to herniation of the pelvic peritoneum through the rectouterine pouch (i.e., posterior vaginal, rectovaginal, cul-de-sac, or Douglas' pouch hernia).

Surgical mesh may also be used to suspend tissues or retract body organs temporarily, e.g., during surgery. For example, U.S. Pat. No. 4,973,300 describes the use of a cardiac sling for supporting the heart during surgery; and U.S. Pat. No. 5,362,294 describes the retraction of body organs such as the uterus or bowel during laparoscopic surgery; U.S. Pat. No. 6,102,921 describes the use of a medical anastomosis sling for the use in repair or regeneration of nerves.

Synthetic mesh materials utilized as slings for the treatment or reinforcement of patient tissues for these and many other conditions can cause patient complications such as erosion, due at least in part to the sharp tangs on the edges of the mesh, which are formed during the manufacturing process or afterward (for example, when a physician cuts or shears or otherwise shapes the material). These tangs can cause an irritative effect which can lead to an erosion when they contact surrounding tissue. Thus, a need exists for a sling which minimizes irritation and erosion of the tissue surrounding the tissue which it supports.

Stress urinary incontinence (SUI), which primarily affects women, is a condition which is successfully treated using surgical slings. Stress urinary incontinence is generally caused by two conditions that may occur independently or in combination, namely, intrinsic sphincter deficiency (ISD) and hypermobility. In ISD, the urinary sphincter valve, located within the urethra, fails to close properly (coapt), causing urine to leak out of the urethra during stressful actions. Hypermobility is a condition in which the pelvic floor is distended, weakened or damaged, causing the bladder neck and proximal urethra to rotate and descend in response to increases in intra-abdominal pressure (e.g., due to sneezing, coughing, straining, etc.), resulting in insufficient response time to promote urethral closure and, consequently, in urine leakage and/or flow.

Biological factors that can affect hypermobility include: poor endopelvic fascia muscle tone (from age or limited activity), endopelvic fascia muscle stretch/tear from trauma (e.g. childbirth), endopelvic fascia/arcus tendenious (muscle/ligament) separation (lateral defect), hormone deficiency (estrogen), concombinant defects (cystocele, enterocele, ureteral prolapse), and vaginal prolapse. Traditional treatment methods include bladder neck stabilization slings in which a sling is placed under the urethra or bladder neck to provide a platform preventing over distention. An emerging alternative treatment is the placement of a mid-urethral sling. Such a sling placement takes advantage of the hypermobillty condition by providing a fulcrum about which the urethra and bladder neck will rotate and provide a "urethral kink" to assist normal urethral closure.

Slings are traditionally placed under the bladder neck to provide a urethral platform limiting endopelvic fascia drop while providing compression to the urethral sphincter to improve coaptation. The mid-urethral placement location provides mechanical stability to a less moveable anatomical structure. Bladder neck slings have traditionally been affixed in the desired location using a bone anchoring method. Mid-urethral slings, being placed in a low mobility area, have demonstrated the effectiveness of an anchorless approach. Recognizing that minimal tension, if any, is necessary, a physician need only place the sling under the mid-urethra secured through the endopelvic fascia to permanently secure the sling in position. The sling permits immediate tissue security through the mesh openings and mesh tangs to initially maintain sling stabilization. As healing occurs, the endopelvic fascia and rectus fascia tissue re-establish vascularity and regrow into and around the knit pattern of the mesh. The sling in this procedure provides a fulcrum about which the pelvic floor will drop (taking advantage of the hypermobility condition of the patient) and a urethral "kink" or higher resistance to obstruct urine flow during high stress conditions.

Thus, while tangs can contribute beneficially to SUI treatment, they can also cause patient complications such as erosion of the vagina or urethra.

SUMMARY OF THE INVENTION

The present invention relates to surgical mesh or slings with a non-tanged (i.e., tangs are unformed, smoothed, rounded, or removed) section disposed on a portion of the sides of the mesh, methods of making such mesh, medical kits including such mesh, and methods of treating a damaged, weakened, sagging, herniated or prolapsed portion of a patient's body using such mesh.

The benefits of such a sling according to the invention include decreased tissue irritation from a non-tanged section when it is in contact with tissue, such as urethral and vaginal tissue, while promoting rapid scar tissue formation around the tanged portion of the sling. The formation of scar tissue generally adds bulk that compresses the tissue to which it is applied (e.g., the urethra), provides support to improve patient continence and inhibits or prevents movement of the placed sling following placement.

In one aspect, the invention involves a sling for use in a medical application. The sling is made of a mesh material that includes first and second opposed ends (i.e., disposed opposite and away from each other) along a longitudinal axis. The mesh material also includes first and second opposed sides separated by a distance along an axis perpendicular to, or substantially perpendicular to, the longitudinal axis. The perpendicular axis intersects the longitudinal axis at the midpoint, or substantially at the midpoint, of the perpendicular axis. A portion of the first and second sides and the first and second ends of the material contains tangs. A portion of the first and second sides does not contain tangs (e.g. tangs on the first and second sides are unformed, smoothed, rounded or removed), creating a non-tanged section. The first and second sides may each have, for example, a non-tanged section about 1 cm to about 5 cm in length, centered along the longitudinal axis.

The sling of the invention may have a shape suitable for a medical application; e.g., it may be rectangular or substantially rectangular. Alternatively, the sling may be octagonal, hexagonal, trapezoidal, elliptical, or some other shape that is suitable to the sling's intended placement location within the body.

In another aspect, the invention relates to a method of making a sling by direct manufacturing with a non-tanged section or by smoothing, rounding or removing the tangs on a portion of the sling to create a non-tanged section.

The sling material provided may be derived from synthetic materials or a combination of mammalian tissue(s) and synthetic material(s). The method of making the sling can further comprise sterilizing the sling material according to methods known in the art so that the sling is suitable for use in various medical applications, and may include packaging the sling in a sterile holder. The sling material may be enclosed within a sleeve to assist in handling the sling and/or to adjust the sling during surgical placement, or to prevent the sling from stretching or becoming misshapen due to handling prior to placement within the body of the patient.

In a further aspect, the invention involves a method of treating a damaged portion of a patient's body using a sling with a non-tanged section. The sling is placed inside the body of a patient such that its perpendicular axis lies substantially along a portion of the patient's body, such as the mid-urethra, bladder, rectum, vagina, blood vessel, nerve, heart, etc.; the material supports a portion of the patient's body in a manner which does not erode the surrounding tissue. The sling may be centered at the damaged portion of a patient's body using the perpendicular axis of the sling as a guide. Pressure may be distributed evenly on a portion of a patient's body with the secured sling material. A surgical fastener such as a suture, a clip, a bone anchor, a staple, or other suitable fastener, may be employed to secure the sling to anatomical structures.

The sling material may be implanted to treat female urinary incontinence according to transvaginal, transabdominal, or combined transvaginal and transabdominal procedures. For example, the method may be employed to treat a patient with SUI, the nontanged section of the sling placed adjacent the patient's mid-urethra.

BRIEF DESCRIPTION OF THE DRAWINGS

In the drawings, like reference characters generally refer to the same parts throughout the different views. The drawings are not necessarily to scale, but rather illustrate the principles of the invention.

DESCRIPTION

Figure 1:
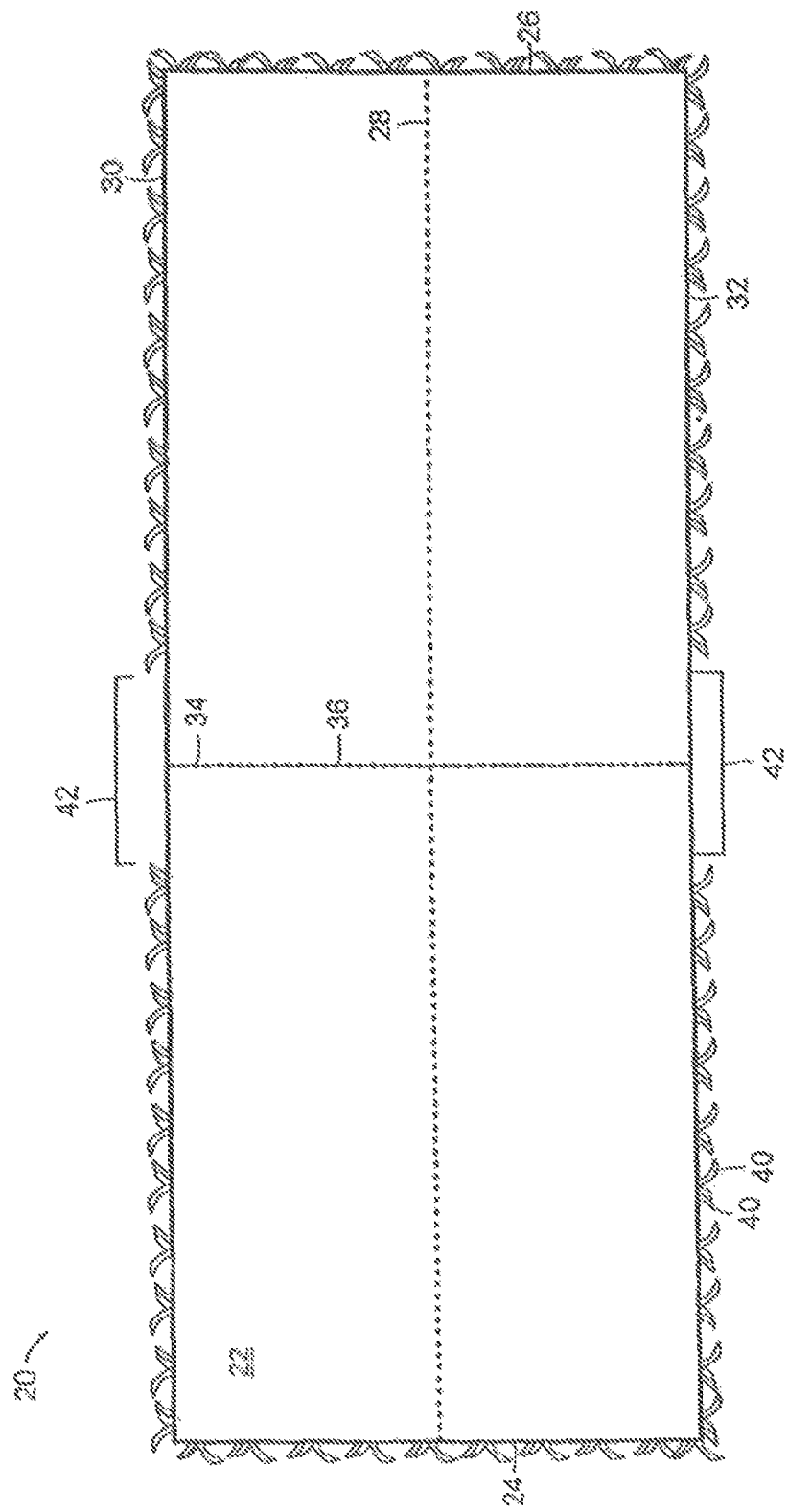
FIG. 1 is a plan view of a rectangular embodiment of a sling having a non-tanged section on either side of the perpendicular axis.

Referring to FIG. 1, a sling 20 in accordance with the present invention can be made of one or more materials 22, and includes a first end 24 and a second end 26. The second end 26 is disposed opposite and away from the first end 24 along a longitudinal axis 28. The material 22 also includes a first side 30 and a second side 32. The second side 32 is disposed opposite and away from the first side 30 along a perpendicular axis 34. The axis 34 is perpendicular to, or substantially perpendicular to, the longitudinal axis 28, and intersects the longitudinal axis 28 at the midpoint, or substantially the midpoint, of the axis 28. The longitudinal axis 28 of the sling 20 may range from about 2.5 cm to about 45 cm in length, while the perpendicular axis 34 may range from about 1.0 cm to about 3.0 cm. The sling is preferably 20 to 30 cm in length and 1 to 3 cm wide, though larger and smaller slings are contemplated depending upon the size of the patient and the surface area of the body part that requires support.

The sling 20 and 21 can be rectangular, as illustrated in FIG. 1, or substantially rectangular in shape (e.g., octagonal). Alternatively, the sling may have another shape (e.g., trapezoidal, hexagonal, or elliptical) suitable to its intended placement location within the body. Exemplary shapes are described in U.S. Pat. No. 6,042,534, the disclosure of which is incorporated herein by reference.

The thickness of the sling material 22 can be uniform over the entire piece of the material or it can vary at one or more different locations. The thickness of sling material 22 may range from about 0.02 to about 0.10 cm, but typically will be about 0.07 cm and have a uniform thickness. The material construction may impact the material thickness and uniformity; for example, a weave may have thicker regions where the fibers intersect.

The mesh may have any of a number of knits, weaves, or braids, such as those described in U.S. Pat. Nos. 5,569,273; 5,292,328; 5,002,551; 4,838,884; 4,655,221; 4,652,264; 4,633,873; 4,520,821; 4,452,245; 4,347,847; 4,193,137; 5,124,136; 3,054,406; and 2,671,444 the disclosures of which are hereby incorporated by reference.

Figure 2:
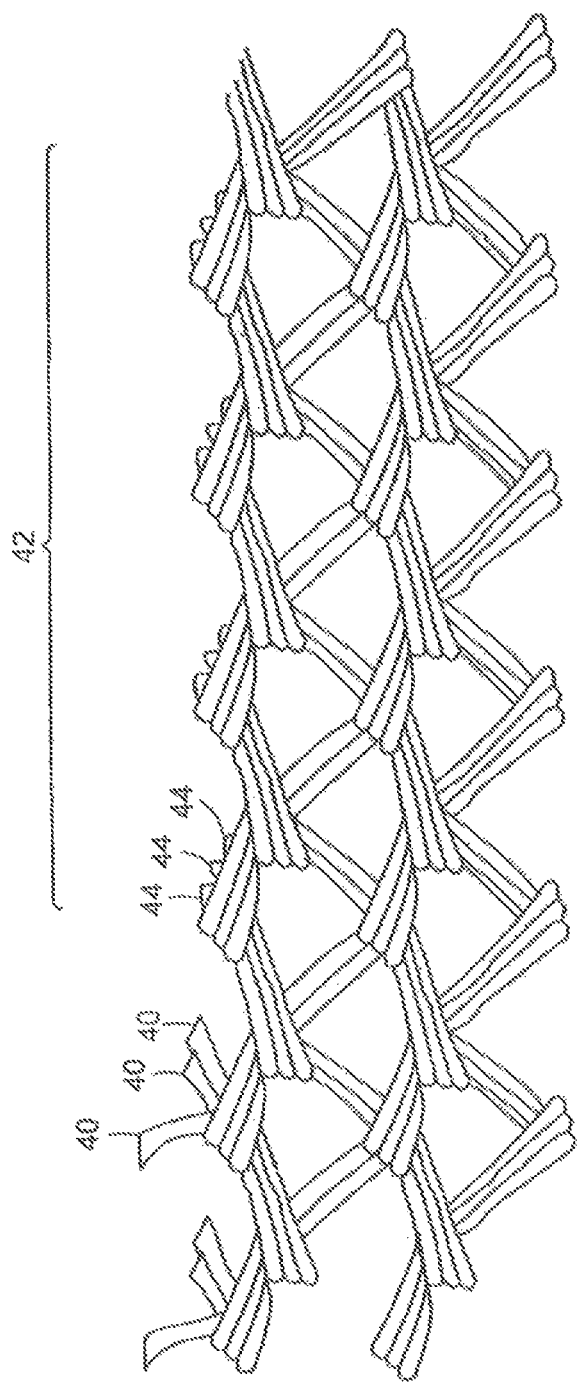
FIG. 2 is a close-up diagram of sling material with a non-tanged section.

The mesh material may be fabricated from any of a number of biocompatible materials such as nylon, polyethylene, polyester, polypropylene, fluoropolymers, copolymers thereof, combinations thereof, or other suitable synthetic material(s). The material may be, for example, a synthetic material that is absorbable by the patient's body. Suitable absorbable synthetic materials include polyglycolic acid, polylactic acid, and other suitable absorbable synthetic materials. The mesh material may be fabricated from one or more yarns, which yarns may be made from one or more materials. The mesh may be produced according to numerous fabrication processes, and may be designed to permit rapid tissue revascularization and tissue in growth by having large interstitial spaces. For example, each yarn of the mesh may have void areas between yarn filaments and the fabrication process may create crevices. An exemplary weave is a tricot knit with two yarns per needle, as illustrated in FIG. 2. In a preferred embodiment, the mesh is composed of polypropylene monofilament yarns.

Absorbable synthetic materials may also be suitable for use in accordance with the invention. Such absorbable synthetic materials include, for example, polyglycolic acid (PGA), polylactic acid (PLA), and other available absorbable synthetic materials. A suitable PGA material is available under the trade designation DEXON, from TYCO. Other suitable polymeric and non-polymeric synthetic materials may be employed in accordance with the invention. Exemplary materials as set forth above are found in U.S. Pat. Nos. 6,090,116; 5,569,273; 5,292,328; 4,633,873; 4,452,245; 4,347,847; 3,124,136; 3,054,406; and 2,671,444, and Inglesia, C. B. et al. (1997) Int. Urogynecol. J. 8:105-115, the entire disclosures of which are incorporated by reference.

Alternatively, the sling material 22 may be derived from a combination of mammalian tissue(s) and synthetic material(s). The mammalian tissue source may be, for example, human, human cadaveric, or tissue-engineered human tissue. The mammalian tissue may alternatively be from an animal source such as porcine, ovine, bovine, and equine tissue sources. Such combinations may also include materials that include both synthetic polymers and animal cells that are treated so as to cross-link the collagen or other commonly antigenic fibers of the animal cells. In one embodiment, at least a portion of the mesh portion of the sling which contacts the patient's tissue comprises a synthetic material requiring smoothness of the tangs.

The tangs (i.e., sharp projections or frayed edges) 40 that form when the material 22 is cut, chopped, torn, frayed or otherwise manufactured may be located along any edge of the material 22. The tangs 40 are generally useful for encouraging tissue growth into the material 22. However, it is found that some tangs 40 may erode the adjacent tissue when the sling 20 is inserted into a patient's body. Accordingly, a portion of the tangs 40 located on sides 30 and 32 (e.g., in some embodiments to within about 1 cm to about 5 cm of either side of the perpendicular axis 34) are therefore unformed, smoothed, rounded or removed to form a non-tanged section 42. By removing these irritative projections, which will be in close proximity to the urethra and anterior vaginal wall, the erosion effects are reduced.

With continued reference to FIG. 1, in one version of the sling, a line 36 is disposed along the perpendicular axis 34 of a rectangular sling 20. The line 36 may be formed by, for example, applying surgical ink along the perpendicular axis 34 of the material 22. Preferably, the approximate midpoint of the non-tanged sections 42 of sides 30 and 32 intersects with line 36. Thus, line 36 may be employed as a visual guide to evenly align the non-tanged sections 42 with the portion of the patient's body that the sling 20 is employed to support.

Any process which will smooth, round or remove the tangs 40 to remove their sharp edges is suitable. For example, the tangs 40 may be heat smoothed by burning or melting. Such a heat process causes melting of the sharp tangs 40 back to the woven knot 44 forming a non-tanged section 42, as shown best in FIG. 2. The non-tanged section 42 may be located on both sides 30 and 32, occupying, for example, about 1 to 4 cm on either side of the perpendicular axis 34. The tangs may be removed, for example, along a 5, 6, 7, 8, 9 or 10 cm portion of the side of the mesh material.

An exemplary method of making a sling 20 of the invention from a material 22, for example, includes manufacturing a sling material 22 and forming a non-tanged section 42 on a portion of a material 22 at sides 30 and 32 adjacent the perpendicular axis 34. The sling 20 may be formed from the cutting to size of a larger piece of sling material 22. The tangs 40 on a portion of each side 30 and 32 are unformed, smoothed, rounded or removed (e.g., to the woven knots) to form a non-tanged section 42. The non-tanged section 42 may span a segment of sides 30 and 32 having a length up to about 4 cm, but usually at least about 1 cm, and the segment is preferably centered on the perpendicular axis 34. In alternative embodiment, the non-tanged section 42 may span a segment of sides 30 and 32 having a length of 5, 6, 7, 8, 9 or 10 cm. In one version of the method, the tangs 40 are smoothed, rounded or removed by exposing the tangs to a source of heat (i.e., by contact or by bringing the heat source into close proximity to the tangs). In an alternative method, a straight blade edge that is heated to a sufficient temperature to simultaneously cut and smooth the tangs 40 may be employed.

The sling 20 may be surrounded by or enclosed within a sleeve or envelope as described in the U.S. patent application entitled "System for Implanting an Implant" co-filed with the instant application, which is hereby incorporated by reference in its entirety. The co-filed application also contains methods for installing slings enclosed within an envelope.

Referring to FIG. 1, the sling 20 may be pre-soaked in a prescribed drug prior to implantation in a patient's body. Exemplary drugs include neomycin, sulfa drugs, antimicrobials, and antibiotics, generally. In some embodiments, the hydrophilic material, the drug, or both when used in combination, release the drug to patient tissues upon contact. Thus, the drugs that are delivered to the patient tissue surfaces when accessing and inserting the sling 20 are active upon contact with the patient's tissue during implantation of the surgical device.

Alternatively, the sling 20 is made of a non-wettable material such as a polypropylene, polyethylene, polyester, polytetrafluoroethylene, TYVEK®, MYLAR®, or copolymers thereof. Polytetrafluoroethylene, which is suitable for use in accordance with the present invention, is available from DuPont (Wilmington, Del., under the trade designation TEFLON®). Such non-wettable materials do not take up any liquids, for example, drugs in solution. In order to permit drugs to bond or absorb to these non-wettable material surfaces, the sling 20 can be treated with a substance that is wettable such as, for example, a wettable coating composition. The wettable coating composition may be a synthetic coating (e.g., polyvinylperilidone or PVP), a natural coating (e.g., collagen) or a physically absorbent material (e.g., sponge comprising cellulose or open celled polyurethane). The wettable coating composition may be hydrophilic, so as to pick up or absorb hydrophilic drugs. Suitable hydrophilic coatings may be water soluble and include, for example, Hydroplus (Boston Scientific Corp., Natick, Mass.), Hydropass (Boston Scientific Corp., Natick, Mass.), hyoscymine sulfate, which is available under the trade designation CYTOSPAZ from Polymedica (Woburn, Mass.), and ketrodac fromethamine, which is available under the trade designation Toradol from Roche Pharmaceuticals (Nutley, N.J.). Hydrophilic drugs that may be employed in accordance with the invention include oxybutynin chloride, lidocaine, ketorolac, and hyoscymine sulfate, for example.

Similarly, a hydrophobic coating may be employed on one or more surfaces of the sling 20. Suitable hydrophobic coatings include but are not limited to hydrophobic coatings that may be employed in accordance with the invention include polytetrafluoroethylene, silicon, and Pyrelene. Such hydrophobic coatings may be used in conjunction with and absorb hydrophobic drugs. Suitable hydrophobic drugs include but are not limited to suitable hydrophobic drugs include ibuprofen, ketoprofen, diclofenac, and lidocaine in hydrophilic form. Where the bonding between these coatings and drugs is weak, the drug that is absorbed will readily release to be delivered to the surfaces it contacts. Alternatively, a stronger bonding affinity may provide a slower timed release of the drug.

Where the coating applied to the surface of the sling 20 has an ionic charge, drugs comprising a complementary charge will bond to the coating when the coating and the drug are exposed to one another. The strength of any bonding will impact how readily the drug is released from the surface of the sling 20. Where the ionic bonding between the coating and the drug is weak, the drug will release more readily. In embodiments where rapid drug release is desirable, covalent bonding between the surface coating and the drug should be avoided.

Alternatively, the sling 20 may be coated with hydrophilic coating 75. The sling 20, coated with hydrophilic coating 75, may be dipped into a solution containing a hydrophilic drug just prior to surgery. In another embodiment, the hydrophilic coating and the hydrophilic drug are mixed to form a single coating. This coating may be disposed on the surface of the sling 20.

Methods of sling delivery and installation, e.g., to treat female stress incontinence include but are not limited to transvaginal, transabdominal (percutaneous), and combined transvaginal and transabdominal procedures.

Variations, modifications, and other implementations of what is described herein will occur to those of ordinary skill in the art without departing from the spirit and the scope of the invention. Accordingly, the invention is not to be limited by the preceding illustrative description.

What is claimed is:

1. A sling for use in a medical application, the sling comprising:
   (a) a first end and a second end, the second end being disposed opposite and away from the first end along a longitudinal axis; and
   (b) a first side and a second side, the second side being disposed opposite and away from the first side by a distance and along an axis that is substantially perpendicular to the longitudinal axis, wherein the first side includes both a tanged portion and a non-tanged portion.

2. The sling of claim 1, wherein the non-tanged portion of first side is about 3 cm and is centered over the perpendicular axis.

3. The sling of claim 2, wherein the non-tanged portion of first side is about 1 cm and is centered over the perpendicular axis.

4. The sling of claim 3, wherein the non-tanged portion of first side is about 0.5 cm and is centered over the perpendicular axis.

5. The sling of claim 1, wherein the non-tanged portion is heat-smoothed.

6. The sling of claim 1, wherein the tanged portion of the first side includes a first tanged portion and a second tanged portion, the non-tanged portion being disposed between the first tanged portion and the second tanged portion.

7. The sling of claim 1, further comprising a visible line disposed substantially along at least a portion of the perpendicular axis as a visual guide.

8. The sling of claim 7, wherein the line comprises a surgical ink.

9. The sling of claim 1, wherein the sling includes synthetic material.

10. The sling of claim 9, wherein the synthetic material is at least one of nylon polyethylene, polyester, polypropylene, fluoropolymers or a co-polymer thereof.

11. The sling of claim 1, wherein the sling has a substantially rectangular shape, and the sling is tanged entirely around a perimeter of the sling except for the non-tanged section on the first side and a non-tanged section on the second side.

12. The sling of claim 1, wherein the sling is surrounded by a sleeve comprising an inner surface and an outer surface.

13. A method of making a sling, the method comprising the steps of:
   providing a material in a shape suitable for a medical application, the material including (a) a first end and a second end, the second end being disposed opposite and away from the first end along a longitudinal axis, and (b) a first side and a second side, the second side being disposed opposite and away from the first side by a distance and along a perpendicular axis that is substantially perpendicular to the longitudinal axis, and that intersects the longitudinal axis at substantially a midpoint thereof, and (c) tangs projecting from the first and second sides; and
   smoothing, rounding or removing the tangs along a portion of the first side and the second side to form a non-tanged section on each side such that each of the first side and the second side includes a tanged section and the non-tanged section.

14. The method of claim 13, wherein said smoothing step is achieved by heat treatment.

15. A method of treating a damaged portion of a patient's body using a sling comprising inserting into a patient at a damaged portion of the patient's body a material including:
   (a) a first end and a second end, the second end being disposed opposite and away from the first end along a longitudinal axis; and
   (b) a first side and a second side, the second side being disposed opposite and away from the first side by a distance and along an axis that is substantially perpendicular to the longitudinal axis, wherein the first side includes both a tanged portion and a non-tanged portion, and the second side includes both a tanged portion and a non-tanged portion.

16. The method of claim 15, wherein the sling is centered at the damaged portion of the patient's body using the perpendicular axis of the sling as a guide.

17. The method of claim 15, wherein pressure is distributed evenly on the damaged portion of the patient's body.

18. The method of claim 15, wherein the patient suffers from stress urinary incontinence.

* * * * *